United States Patent
Epstein et al.

(10) Patent No.: US 7,604,620 B2
(45) Date of Patent: Oct. 20, 2009

(54) METHODS FOR DIRECTLY INJECTING PLUG FORMING MATERIALS FROM A CATHETER

(75) Inventors: Samuel J. Epstein, Lynnfield, MA (US); Wendy Naimark, Cambridge, MA (US); Tim Mickley, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 332 days.

(21) Appl. No.: 11/636,638

(22) Filed: Dec. 11, 2006

(65) Prior Publication Data
US 2007/0106259 A1 May 10, 2007

Related U.S. Application Data

(63) Continuation of application No. 10/078,676, filed on Feb. 21, 2002, now Pat. No. 7,169,127.

(51) Int. Cl.
*A61M 5/00* (2006.01)
(52) U.S. Cl. ...................... 604/264; 604/117
(58) Field of Classification Search ......... 604/508–510, 604/264, 268, 272, 164.01, 164.04, 164.08
See application file for complete search history.

(56) References Cited

U.S. PATENT DOCUMENTS

| 5,237,993 A | | 8/1993 | Skrabal |
| 5,725,521 A | | 3/1998 | Mueller |
| 5,752,944 A | * | 5/1998 | Dann et al. ............... 604/352 |
| 5,758,663 A | | 6/1998 | Wilk et al. |
| 5,827,247 A | * | 10/1998 | Kay ........................ 604/327 |
| 5,944,716 A | | 8/1999 | Hektner |
| 6,042,565 A | | 3/2000 | Hirschman et al. |
| 6,045,565 A | | 4/2000 | Ellis et al. |

(Continued)

FOREIGN PATENT DOCUMENTS

WO      WO 00/67655      11/2000

(Continued)

OTHER PUBLICATIONS

Bio, Jialin et al., Catheterization and Cardiovascular Interventions, 53-429-434, Intramyocardial Delivery of FGF2 in Combination with Radio Frequency Transmyocardial Revascularization, 2001 Wiley-Liss, Inc.

(Continued)

*Primary Examiner*—Nicholas D Lucchesi
*Assistant Examiner*—Rebecca E Eisenberg
(74) *Attorney, Agent, or Firm*—Vidas, Arrett & Steinkraus

(57) ABSTRACT

The present invention relates to the direct delivery of therapeutic to a target tissue. In one embodiment a method for direct injection of plug forming material into a body tissue is provided. The method may comprise providing a catheter including an injection tube having a first channel, a second channel and a piercing tip. The first and second channels can be in fluid communication with a pressure source and a plug forming material. The injection tube may be slidably positioned in a pressure apron and moved from a first position to a second position so that the piercing tip extends beyond the tissue-mating surface in the second position to deliver the plug forming material.

14 Claims, 6 Drawing Sheets

U.S. PATENT DOCUMENTS

| | | |
|---|---|---|
| 6,102,926 A | 8/2000 | Tartaglia et al. |
| 6,152,918 A | 11/2000 | Padilla |
| 6,193,763 B1 | 2/2001 | Mackin |
| 6,224,566 B1 | 5/2001 | Loeb et al. |
| 6,231,568 B1 | 5/2001 | Loeb et al. |
| 6,319,230 B1 | 11/2001 | Palasis et al. |
| 6,331,178 B1 | 12/2001 | Loeb et al. |
| 6,488,659 B1 | 12/2002 | Rosenman |
| 6,508,802 B1 | 1/2003 | Rosengart et al. |
| 6,582,400 B1 | 6/2003 | Hawk et al. |
| 6,595,958 B1 | 7/2003 | Mickley |
| 6,616,626 B2 | 9/2003 | Crank et al. |
| 6,620,139 B1 | 9/2003 | Plicchi et al. |
| 6,749,617 B1 | 6/2004 | Palasis et al. |
| 6,796,963 B2 | 9/2004 | Carpenter et al. |
| 6,939,322 B2 | 9/2005 | Crank et al. |
| 6,964,649 B2 | 11/2005 | Goll |
| 2002/0193732 A1 * | 12/2002 | Naimark et al. ............... 604/84 |
| 2003/0083607 A1 | 5/2003 | Bobo |
| 2005/0124975 A1 | 6/2005 | Law |

FOREIGN PATENT DOCUMENTS

| | | |
|---|---|---|
| WO | WO 01/10313 | 2/2001 |
| WO | WO 01/89606 | 11/2001 |

OTHER PUBLICATIONS

Grossman, P. Michael, et al., Rentention of Myocardial Injectate After Direct Surgical or Catheter-Based Needle Adminstration, Mar. 1, 2000, Abstract No. 870-1.

FMC BioPolymer, Biotechnology, Mar. 1990, vol. 8, No. 3)74).

* cited by examiner

METHODS FOR DIRECTLY INJECTING PLUG FORMING MATERIALS FROM A CATHETER

CROSS-REFERENCE TO RELATED APPLICATIONS

This application is a Continuation of application Ser. No. 10/078,676, filed Feb. 21, 2002 now U.S. Pat. No. 7,169,127.

FIELD OF THE INVENTION

The present invention relates to the direct delivery of therapeutic to a target tissue. More specifically, the present invention relates to an injection device and methods that employ a pressure apron that can sealably engage a target tissue during the introduction of therapeutic to the target tissue.

BACKGROUND OF THE INVENTION

Therapeutics are often delivered directly to target areas of diseased tissue in various contemporary medical procedures. This direct delivery has proven to be an advantageous approach when treating numerous medical conditions. One advantage of this procedure is that only the target tissue may be exposed to the therapeutic, while another is that a controlled dose of therapeutic may be directly delivered to the target tissue.

Due to innumerable variables including viscosity of the therapeutic, receptivity of the target tissue, and the active contraction and expansion of the target tissue, therapeutic delivered to a target site may not remain in place both during and after its delivery. It may, instead, diffuse away, being leaked or ejected from the area surrounding the delivery point. Specifically, for example, when therapeutic is injected into an actively contracting tissue such as the myocardium of the heart, the therapeutic may be ejected or squeezed out through its point of entry by the repeated expansion and contraction of the heart muscle. This unintended and unwanted leakage can result in an unascertainable dosage of therapeutic being delivered and arbitrary interaction between leaked therapeutic and neighboring tissue and muscle.

SUMMARY OF THE INVENTION

An injection catheter for direct injection into a body tissue is provided in one embodiment of the present invention. In this embodiment the injection catheter may include an injection tube having a first channel and a piercing tip, the first channel in fluid communication with a pressure source. Furthermore, the injection catheter may also include a pressure apron with a tissue-mating surface, wherein the injection tube can extend beyond the tissue-mating surface in at least certain positions.

In another embodiment a medical kit for delivering a therapeutic is provided. This medical kit may include a catheter having a channel and a piercing tip, the piercing tip in fluid communication with a pressure source, the piercing tip slidably placed in the channel. The catheter in this embodiment may include a pressure apron with a tissue-mating source. A therapeutic may be included with the kit as well.

A system for preventing leakage of material from a body tissue during the injection of a therapeutic may be provided in yet another embodiment. A system in accord with this embodiment may include a catheter with a channel, a pressure apron surrounding the channel, and a piercing tip retractably positioned within the channel, the pressure apron having a tissue-mating surface.

DETAILED DESCRIPTION

Figure 1:
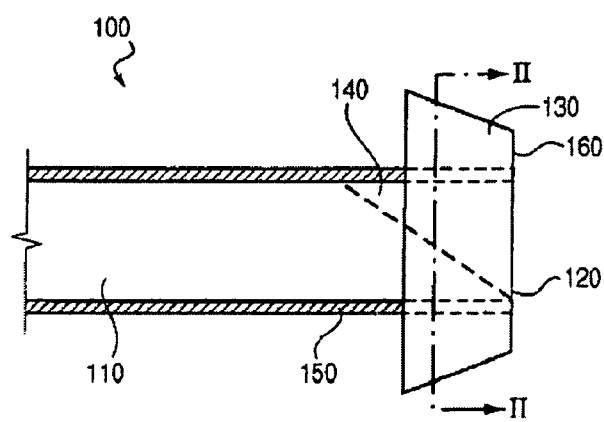
FIG. 1 is an enlarged partial cross-sectional view of a single channel injection catheter having an injection tube with a piercing tip in accord with an embodiment of the present invention.

FIG. 1 is an enlarged partial cross-sectional side view of a single channel or lumen injection catheter 100 having a pressure apron 130 in accord with an embodiment of the present invention. In the embodiment of FIG. 1 a single channel injection tube 110 is enclosed by catheter wall 150 of the catheter 100 and shares a concentric longitudinal axis with the catheter 100. The single channel injection tube 110 in this embodiment has a tapered end terminating in a piercing tip 120. Also labeled in this figure are the internal lumen 140 of the catheter 100 and the tissue-mating surface 160 of the pressure apron 130.

The injection catheter 100 in this embodiment may be used to deliver therapeutic and in-situ plug forming material to a target site. Accordingly, in one embodiment, the single channel injection tube 110 may be coupled to a pressure source, such as a pump or a syringe that can be used to force therapeutic and in-situ plug forming material down the internal channel of the injection tube 110 to a target site. This therapeutic and plug forming material may be fed into the channel during the medical procedure or beforehand. If it is delivered during the procedure, it may be directly injected into the pump being used as a pressure source. Alternatively, if it is preloaded, it may be loaded just prior to the initiation of the procedure or sometime earlier than that. As described in greater detail below, the therapeutic being delivered may be one of numerous available therapeutics and the in-situ plug forming material may include an alginate and calcium, as well as numerous other plug forming compounds. The term "therapeutic" as used herein refers to therapeutic materials, and includes such non-limiting examples as therapeutic polynucleotides, proteins, and polypeptides. The term "therapeutic" as used herein, is synonymous with the term "therapeutic materials."

The injection catheter 100 in this embodiment may be used to deliver therapeutic to a target site located deep within the body. Consequently, it may be preferable to form the catheter 100 and the injection tube 110 from suitably rigid materials that will allow sufficient control but remain flexible so that they may be maneuvered within the body by the medical practitioner performing the procedure. Such suitable materials may include fabricating the catheter wall 150 and injection tube 110 from a rigid polymer while making the piercing tip 120 from a more rigid material such as nitinol so that it may readily pierce into target tissue.

Surrounding the catheter 100 in this embodiment is a pressure apron 130. This pressure apron 130 has a tissue-mating surface 160 that may sealably engage a target tissue during use. In order to promote a tight seal with a target tissue this tissue-mating surface may have an adhesive placed on it and it may be configured or adapted to promote its sealing engagement with a target tissue. For instance, this adaptation may include adding a profiled surface to the pressure apron and forming it in the shape of a suction cup, both of which can enhance its ability to engage the target tissue. In either case, it is preferable that the pressure apron does not have pointed edges that can snare or damage a lumen wall when the catheter is being snaked to the target site. The adhesive placed on the tissue-mating surface may be selected from polysaccharides, cellulose, hydrogels, alginate, or combinations thereof.

Rather than being two discrete structures, the pressure apron 130 and the catheter wall 150 may also be formed from the same material. In either case, it is preferable that the materials chosen be sufficiently rigid to provide for catheter control, while at the same time being sufficiently flexible to allow for maneuverability during the procedure and sealability with the target tissue.

Figure 2:
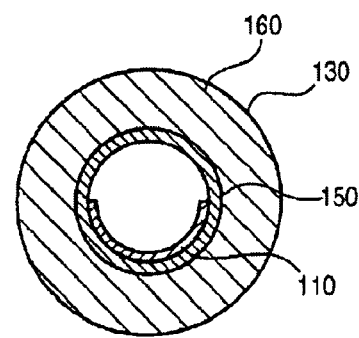
FIG. 2 is a sectional view along line II-II of FIG. 1.

FIG. 2 is a cross-sectional view taken along line II-II of FIG. 1. In FIG. 2 the catheter wall 150, pressure apron 130, and injection tube 110 can be seen. While the cross-section in this view makes it clear that the lumen and the channel are circular these structures could have other cross-sectional configurations including oval, stellate, rectangular, and side-by-side or round orientations.

Figure 3:
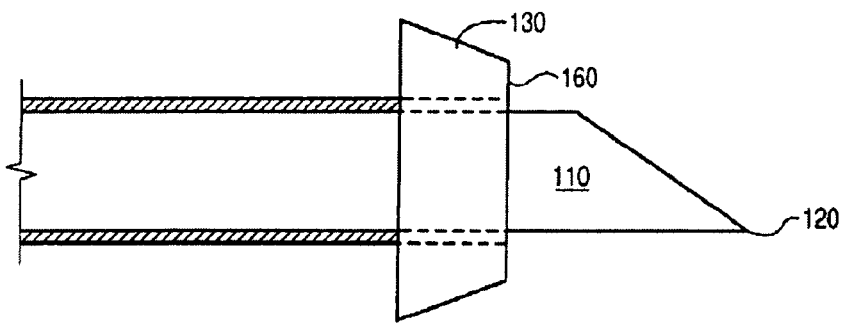
FIG. 3 is a partial cross-sectional view of the injection catheter of FIG. 1, with the injection tube extending from the pressure apron.

FIG. 3 is a side partial cross-sectional view of the catheter from FIG. 1. In FIG. 3 the injection tube 110 is shown protruding from the tissue-mating surface 160 of the pressure apron 130 as may occur during the deployment of therapeutic to a target tissue in the body. As can be seen in FIG. 3, the most distal point of the injection tube 110 forms the piercing tip 120.

The pressure apron 130 in this embodiment can be formed of biocompatible polymeric or metallic materials. Examples of the materials that can be used to form the pressure apron 130 include silicones, nylons, urethanes, polyamides, polyimides, elastomers, nitinol, surgical stainless steel, biopolymers (including extracellular matrix derivatives [cellular or acellular] with elastin, collagen, glycosaminoglycan and other constituents either in combination or separately), and/or combinations thereof. Moreover, while the pressure apron 130 is shown in the shape of a truncated cone it may also be formed in other shapes as well including a cylinder, a disk and any other shape that has a tissue-mating surface.

In use, the tissue-mating surface 160 of the pressure apron 130 may be guided by a practitioner to a target tissue to be treated. Once the surface 160 reaches the target tissue it may be forcibly pushed into the target tissue. Then, once the surface 160 is in position, the injection tube 110 may be forced or urged into the target tissue. After entering the target tissue a therapeutic and plug forming material, compound or agent may be pushed down through the injection tube 110 until it emerges from the channel at its distal end. As the compound is ejected from the tube 110 the tube 110 may be drawn back towards the pressure apron 130 leaving a void that the compound can fill. Still further, in a single use embodiment the pressure apron may become dislodged after the injection has occurred and may remain at the target site and serve as a patch.

In a preferred embodiment the tube 110 will be withdrawn into the pressure apron 130 after the entire void has been filled with compound. During this time the pressure apron 130 will remain in place with the tissue-mating surface 160 sealably engaging the target site. It should preferably remain there until such time as the compound has hardened to form an in-situ plug. Once formed, the pressure apron 130 may then be withdrawn and the procedure repeated at a different point if necessary. To facilitate the adhesion of the tissue-mating surface 160 to the target tissue an adhesive may be used, a vacuum force may be applied, the pressure apron 130 may be shaped in the form of a suction cup to sealably engage the tissue-mating surface 160 to target tissue. Other methodologies may be used as well.

The plug forming material and the therapeutic may be urged down the injection tube 110 channel through various means including a syringe, a mechanical pump, and a squeezable bladder—each means located upstream of the distal end of the piercing tip 120. These means may be used not only to push the plug forming material and the therapeutic through the injection tube 110, but also to store the plug forming material and the therapeutic prior to their use. Likewise, these means can be used to control the volume and rate of injection of the plug forming material and the therapeutic.

As noted above, the catheter 100 in this embodiment can be made from any suitably rigid material including rigid plastics. Similarly, the injection tube 110 can also be made from any suitably rigid material capable of carrying fluids. In either case, if the material can come in contact with a therapeutic or an in-situ plug forming compound it is preferable that the material be compatible with the therapeutic and compound.

In the embodiment of FIGS. 1-3, the catheter 100 is fixed to the pressure apron 130. Alternatively, the catheter 100 may be slidable within the pressure apron 130 so that it can be slid back and forth through the pressure apron 130 and extended from the pressure apron 130 as necessary during a medical procedure. Similarly, the injection tube 110 may be extended from the pressure apron 130 in various degrees or lengths depending on the required depth of injection.

In the present embodiment, as well as in other embodiments, the therapeutic can be a polymer solution. Moreover, in the dual lumen or channel systems described below the polymer may include alginate, while the plug forming material can be, for example, a plug forming cross-linking agent such as calcium. Additional possible plug forming materials in dual lumen systems can include, but are not limited to, for example, fibrin formed through an enzymatic-catalyzed reaction of thrombin and fibrinogen, and sucrose acetate isobutyrate formed by the removal of ethanol in an in-vivo aqueous environment thereby precipitating a polymer.

The therapeutic traveling through the injection tube 110 in this embodiment, as well as in the other embodiments, may also include, for example, pharmaceutically active compounds, proteins, cells, oligonucleotides, ribozymes, antisense oligonucleotides, DNA compacting agents, gene/vector systems (i.e., any vehicle that allows for the uptake and expression of nucleic acids), nucleic acids (including, for example, recombinant nucleic acids; platelets, dextran, glycosamino glycans, carbohydrates; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, interleukin-10, serine protease inhibitor, estrogen, sulfasalazine, acetylsalicylic acid, and mesalamine; calcium entry blockers such as verapamil, diltiazem and nifedipine; antineoplastic/antiproliferative/antimitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, antithrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasocactive mechanisms; survival genes which protect against cell death, such as anti-apoptotic Bcl-2 family factors and Akt kinase; and combinations thereof. Myoblasts, bone marrow derived stem cells, mesenchymal stem cells, and endothelial progenitor cells may also be used. Moreover, cells can be of human origin (autologous or allogenic) or from an animal source (xenogeneic), genetically engineered if desired to deliver proteins of interest at the injection site. The delivery mediated is formulated as needed to maintain cell function and viability.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor .alpha. and .beta., platelet-derived endothelial growth factor, platelet-derived growth factor, tumor necrosis factor .alpha., hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

Organs and tissues that may be treated by the methods of the present invention include any mammalian tissue or organ, whether injected in vivo or ex vivo. Non-limiting examples include heart, lung, brain, liver, skeletal muscle, smooth muscle, kidney, bladder, intestines, stomach, pancreas, ovary, prostate, eye, tumors, cartilage and bone.

The therapeutics can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

FIGS. 4A through 4D each show cross-sectional views of a tissue target 400 and a dual channel injection catheter 470 as being employed in accordance with another embodiment of the present invention. These figures show sequential steps beginning with the placement of the catheter 470 against the target tissue, the formation of the in-situ plug 494, and the release of therapeutic to the surrounding area.

Figure 4B:
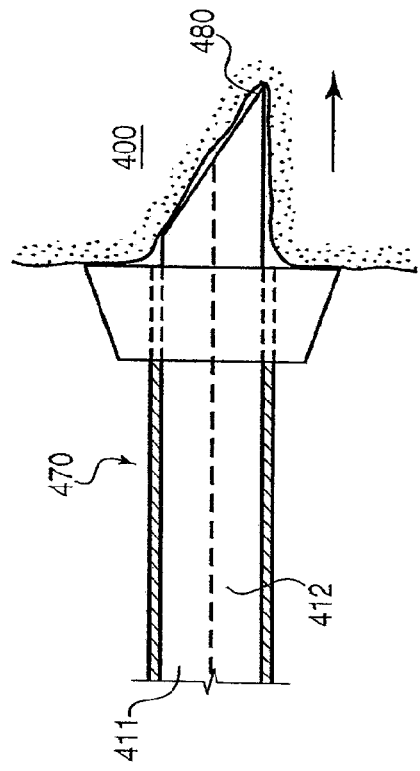
FIGS. 4A through 4D each show partial cross-sectional views illustrating individual steps of a method of using a dual-channel injection catheter in accord with another embodiment of the present invention.
Figure 4D:
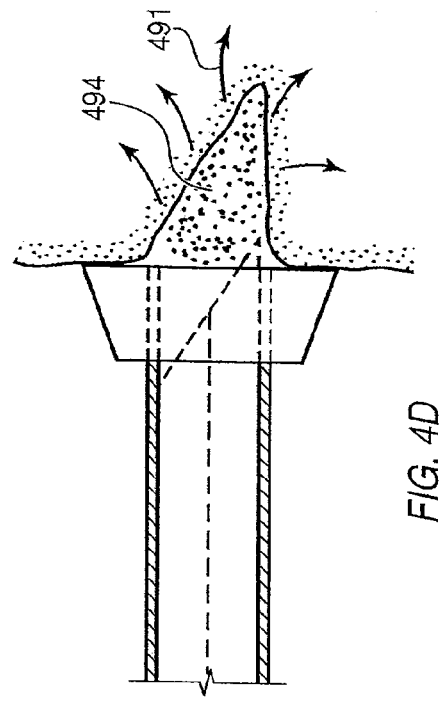
Figure 4A:
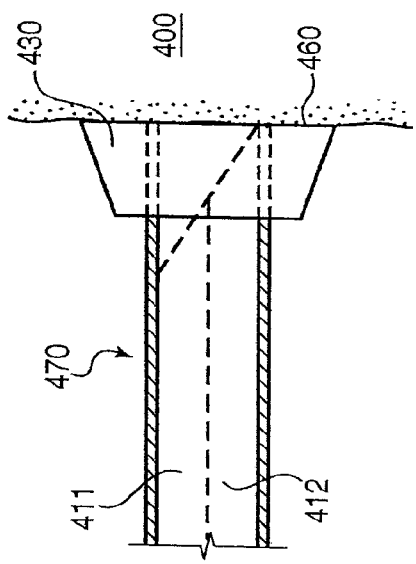

In FIG. 4A, the dual channel injection catheter 470 is shown following its placement against the target tissue 400 such that the pressure apron 430 is preferably sealably engaging the target tissue 400. FIG. 4A further shows the first and second channels 411, 412 positioned within the catheter prior to their insertion into the target tissue 400. Also visible in FIG. 4A is the preferred orientation of the pressure apron 430 wherein the larger side 460 of the pressure apron 430 is outwardly facing.

FIG. 4B shows the dual channel injection catheter 470 with the first channel and second channels 411 and 412 being urged through the pressure apron into the target tissue 400. As can be seen, the piercing tip 480 of the second channel 412 has penetrated into the target tissue 400 to form a void 475 in the target tissue 400. As can also be seen the first channel 411 and the second channel 412 have moved in tandem. Alternatively, in other embodiments, these channels may move independently as needed.

Figure 4C:
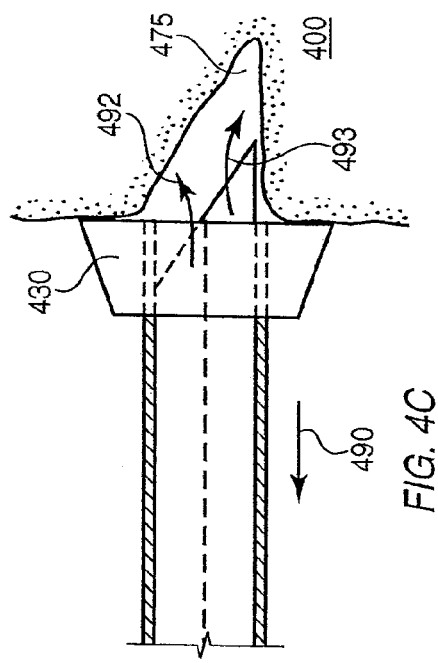

Next, in FIG. 4C, the first and second channels have been partially retracted out of the target tissue 400 in the direction of arrow 490. During this step, as can be seen, the pressure apron 430 has remained sealably engaged with the target tissue 400. Also, as indicated by arrows 492 and 493, in-situ plug forming material and therapeutic are being injected into the void 475 during this step.

Dependent upon the properties of the plug forming material and the therapeutic, they may each be concurrently ejected as the injection tube 410 is withdrawn. They may also be delivered only after the injection tube 410 has reached its fully retracted position. Their fully retracted position is shown in FIG. 4D, which also shows the plug in a fully formed state releasing therapeutic to the target tissue as indicated by arrows 491. Once the plug 494 has been formed the pressure apron 430 may be removed. The plug forming or cross-linking agent injected into the void can be any one of numerous plug forming materials including calcium and thrombin.

Figure 5:
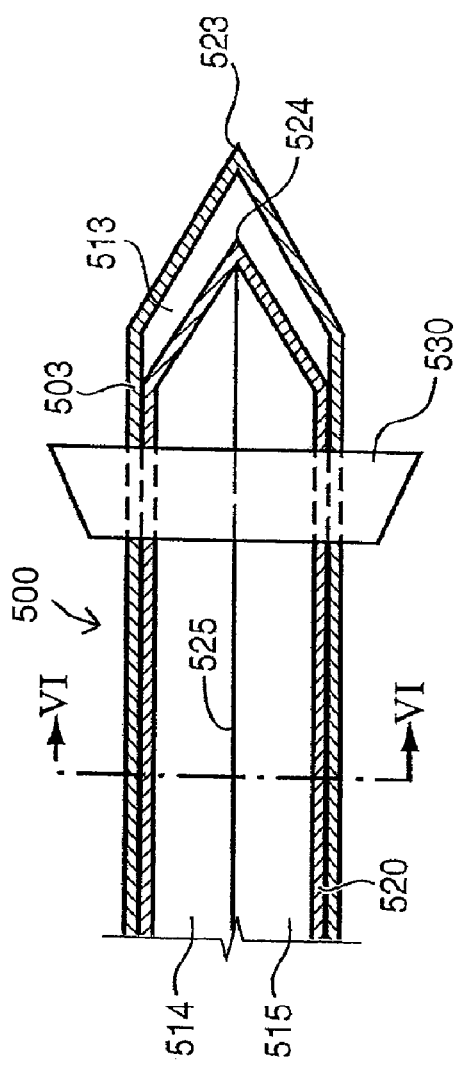
FIG. 5 is a side partial cross-sectional view of a dual-channel injection catheter in accord with yet another embodiment of the present invention.

FIG. 5 is an enlarged side view of a dual-channel injection catheter system 500 according to another alternative embodiment of the present invention. In this embodiment, an outer catheter 503 has a lumen 513 and contains an injection tube 520 having first and second channels 514 and 515. Both the injection tube 520 and the catheter 503 end in piercing tips 524 and 523. The catheter is surrounded by pressure apron 530 in this embodiment.

The outer catheter 503 may be slidably positioned within the pressure apron 530 in this embodiment. Therefore, it may be used to form the void for the therapeutic with its piercing tip 523 and may then be retracted back before the piercing tip 524 of the first and second channels is advanced further into the target tissue. In order to provide for a sealable engagement with the target tissue, if the outer catheter 503 is slidable within the pressure apron, it should be lockable within the apron in its retracted position so that an adequate amount of force may be placed on the pressure apron by the catheter system 500 to maintain a seal with the target tissue.

The first and second channels 514 and 515 may be independently moveable and can be extended from and retracted into the pressure apron 530 individually or in tandem as required by the procedure being performed. For instance, in one embodiment, after the pressure apron 530 has been placed up against a target tissue, both the first channel 514 and the second channel 515 may be concurrently advanced into the target area. Then, a plug forming matrix, compound, or material may be injected from the first channel 514 while the second channel 515 remains fully extended into the tissue. After the plug forming matrix has been allowed to set up, therapeutic may then be ejected from the second channel 515 into the plug forming matrix as the second lumen is retracted from the target area. By fabricating the plug in this fashion, the therapeutic can be interfaced with the plug forming matrix after it has begun to set up rather than in conjunction with it. Once the in-situ plug has formed the pressure apron 530 may then be removed from the target area and the procedure may be repeated.

In the present embodiment, as with the others and as suggested above, the therapeutic can be a polymer solution including, for example, alginate, while the plug forming material can be, for example, a plug forming, cross-linking agent such as calcium. Additional possible plug forming materials can include, but are not limited to, for example, fibrin, formed through an enzymatic-catalyzed reaction of thrombin and fibrinogen, and sucrose acetate isobutyrate formed by the removal of ethanol in an in-vivo aqueous environment thereby precipitating a polymer.

Figure 6:
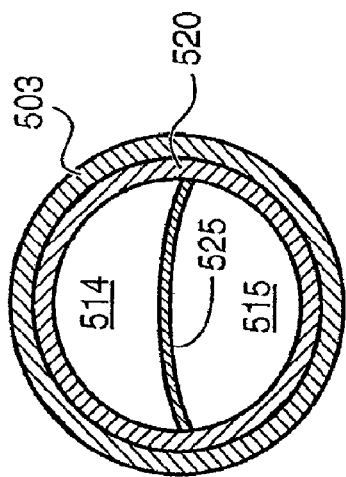
FIG. 6 is a cross-sectional view along line IV-IV of FIG. 5.

FIG. 6 is a cross-sectional view of the dual channel injection catheter of FIG. 5 taken along line IV-IV showing one possible arrangement of the first channel 514 and the second channel 515. In FIG. 6, the second channel 515 is shown to be larger than the first channel 514. However, in an alternate embodiment the first and second channels can be the same size. Additionally, while the first and second channels are shown longitudinally side by side, in alternate embodiments, any arrangement can be used, including, for example, having one channel surrounding the other. Furthermore, the present invention is not intended to be limited to one or two channel injection tubes, as three or more may also be employed. Likewise, the channels and lumens need not be concentric but may also be positioned side by side and in other orientations as well.

Figure 7:
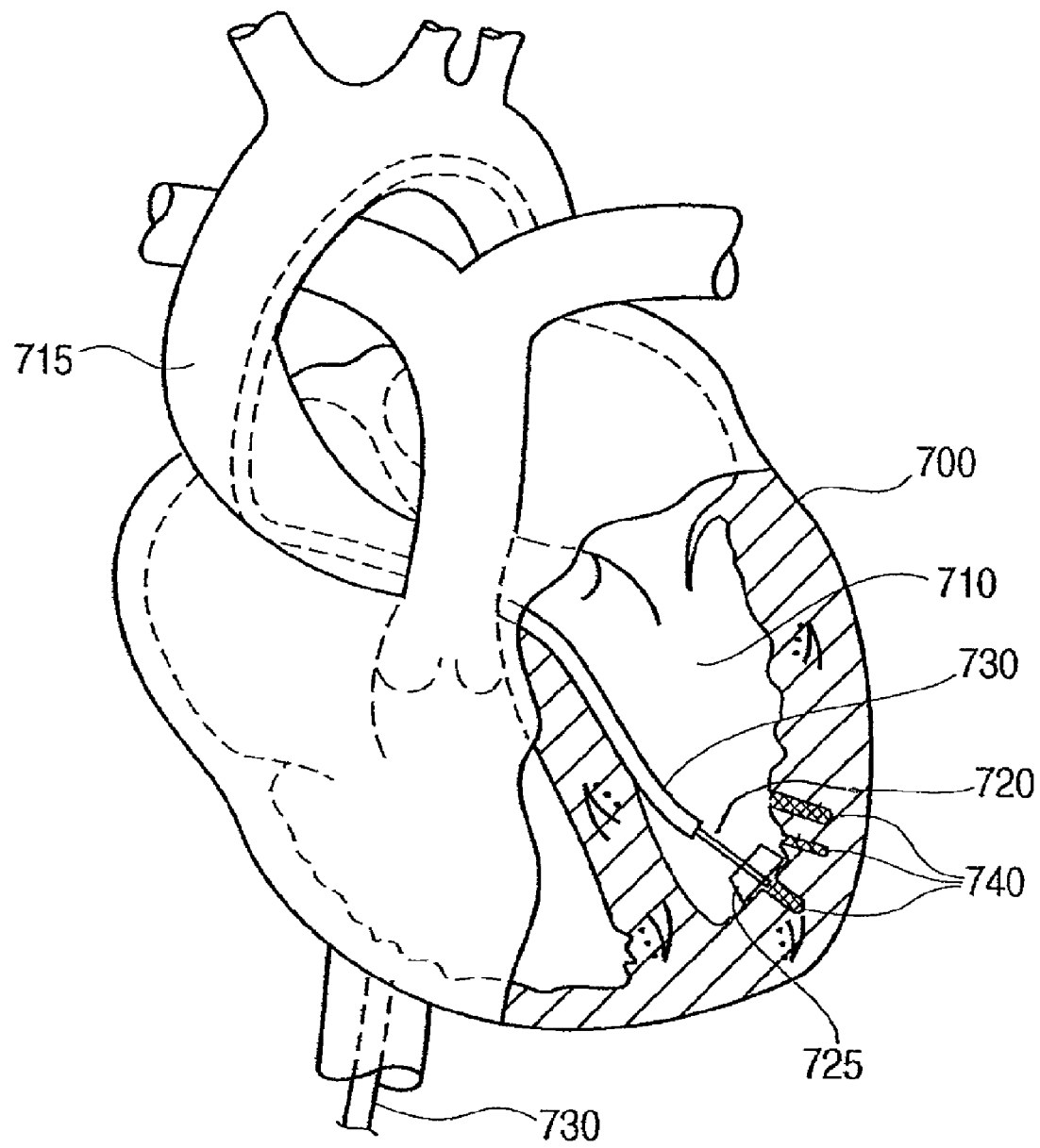
FIG. 7 is a partial cross-sectional view of a human heart including an injection catheter in accord with another embodiment of the present invention.

FIG. 7 shows a cross-sectional view of a human heart 700 with one embodiment of the present invention located therein. In FIG. 7 the injection catheter 730 having a piercing tip 720 and a pressure apron 725 threaded through an aortic artery 715 into the left ventricle 710 of the heart 700 can be seen. While the injection catheter is shown threaded through the aortic artery, it may also be threaded through the femoral, brachial, and carotid artery.

In-situ plugs 740, formed in accordance with the present invention can be clearly seen in FIG. 7.

Figure 8:
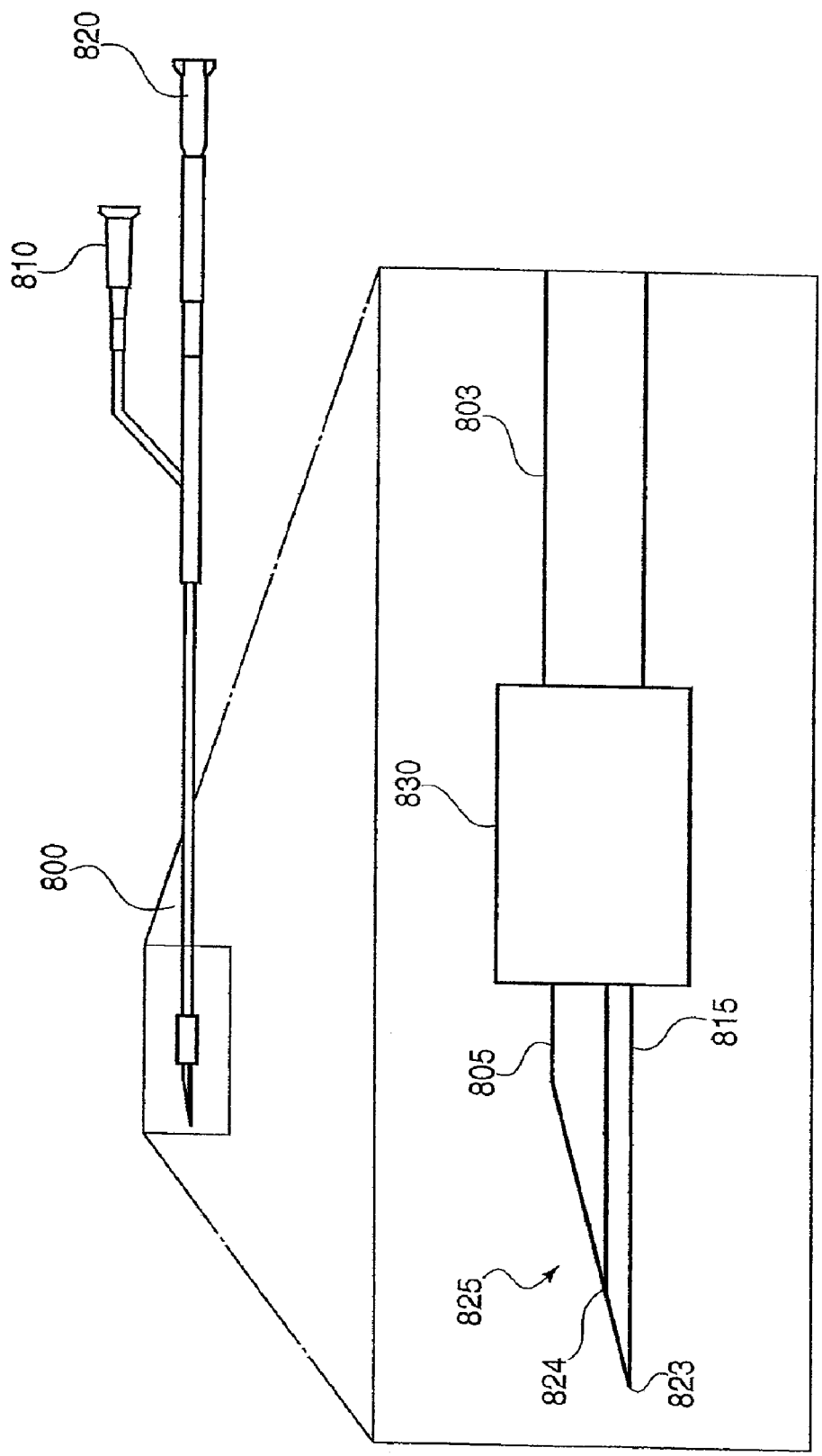
FIG. 8 is a side view of a dual-channel injection catheter in accord with another embodiment of the present invention.

FIG. 8 shows a side view of another alternative embodiment of the present invention. Visible in FIG. 8 is the catheter 800, the first channel feed 810, the second channel feed 820, catheter wall 803, pressure apron 830, first channel 805, second channel 815, piercing tip 823, injection tube 825, and piercing tip 824. In this embodiment the pressure apron is shown as a metal cylinder and the channel feeds, which allow for the insertion of therapeutic and plug forming material, are positioned at the proximal end of the catheter.

Figure 9:
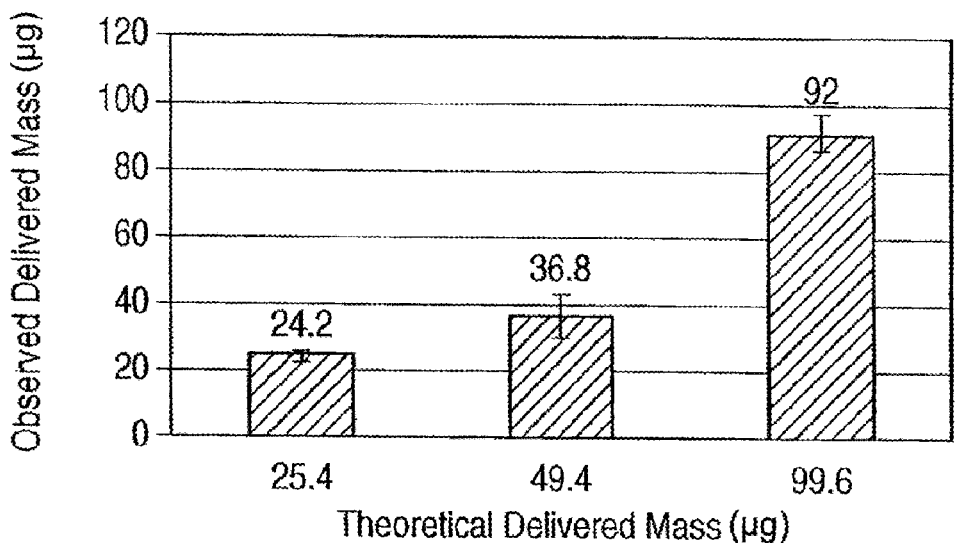
FIG. 9 is a graph of a scaling group showing theoretical delivered mass versus observed delivered mass.

The use of in-situ plugs to deliver large molecules in accord with the present invention has been proven to be a plausible method of delivery. FIG. 9 is a graph of a scaling group, proving this, showing theoretical delivered mass versus observed delivered mass. In FIG. 9, results are presented for a three solution scaling group used in a direct injection FITC-Dextran delivery scaling test. The three solutions had theoretical delivered masses of 25.4, 49.4 and 99.6 micrograms (μg) as shown along the x-axis of FIG. 9. The observed delivered masses for the three solutions are 24.2, 36.8 and 92 μg, respectively, as shown along the y-axis.

Figure 10:
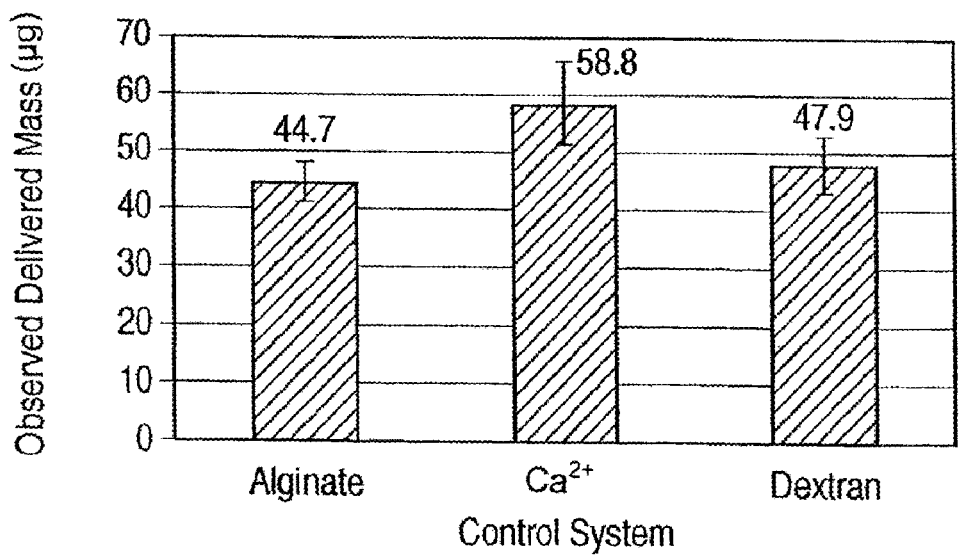
FIG. 10 is a graph of a control group showing a control system versus observed delivered mass.

FIG. 10 is a graph of a control group, also addressing the issue of therapeutic delivery, showing a control system versus observed delivered mass. In FIG. 10, results are presented for a three solution control group used in a direct injection FITC-Dextran delivery controls test. The controls used included Alginate, Ca2+ and Dextran. Each of the three solutions had theoretical delivered masses of 50 μg as shown along the x-axis of FIG. 10. The observed delivered masses for the three solutions are 44.7, 58.8 and 47.9 μg, respectively, as shown along the y-axis.

The test procedure followed to obtain the scaling group and control group results shown in FIG. 9 and FIG. 10 was designed to verify whether the concentration of released agent is equal to the expected. Specifically, the procedure involved the following steps: Prepare 40 g of a 2.5% (w/w) Alginate solution (aqueous).

1. Prepare a 0.6M $CaCl_2$ solution (aqueous).
2. Prepare an agarose gel:
   In a 50 ml beaker mix 2.5% (w/w) agarose with water.
   Heat agarose mixture in a microwave until steadily boiling. (Solution should be completely clear.)
   Using heat-protective glove(s), remove the beaker from the microwave and pour the hot gel into a tin weighing pan until the liquid level is almost to the top of the weighing pan.
   Cover the gel and allow it to cool for 30 minutes. (The gel should be used on the same day it is made.)
3. 
   Prepare FITC-Dextran injection solutions according to the following chart:

| Solution Number | [Dextran] (mg/ml) | Mass Dextran (mg) | Volume Alginate (mL) | Volume $CaCl_2$ (mL) | Volume Water (mL) |
|---|---|---|---|---|---|
| 1 | 2.5 | 12.5 | 5 | — | — |
| 2 | 5 | 25 | 5 | — | — |
| 3 | 10 | 50 | 5 | — | — |
| 4 | 5 | 25 | — | 5 | — |
| 5 | 5 | 25 | — | — | 5 |
| 6 | 5 | 25 | 5 | — | — |

1. In a darkened room load approximately 100 μl of the $CaCl_2$ solution and 100 μl of the Alginate solution into their respective syringes.
2. Prepare for injection by dispensing both materials until each is just about to emerge from the tip of the catheter (approximately the void volume shown above).
3. Insert the needle tip into the agarose gel until pressure apron is firmly set against surface of gel.
4. Dispense 10 μl of the Alginate and 2 μl of the $CaCl_2$ and quickly remove needle from gel.
5. Visually inspect for plug placement.
6. Remove syringes and flush each needle with water and air.
7. Reload and repeat these steps (n=3 for each solution).

The analysis of the results from the above tests involved:

Using a razor blade to cut a cube out of the gel approximately 0.5 cm around the injection site.
1. Cut 2 mandrels such that they can fit into a 20 mL scintillation vial.
2. Use 2 mandrels in tandem to break up the agarose cube within a 20 mL vial.
3. Leave the mandrels in the vial and fill with 10 mL PBS.
4. Cap the vial and allow the contents to incubate under agitation and light cover for 17 to 24 hours.
5. Aliquot 200 mL from each vial for fluorometry.
6. Fluorometry is set for 490 nm excitation and 520 nm emission.

An injection catheter device and a method for delivering a therapeutic that can form into a plug in-situ are provided. Various embodiments of the injection catheter and methods of use thereof are described above including a catheter having a first lumen in fluid communication with a pressure source and a piercing tip, and a pressure apron having a tissue-mating surface for sealably engaging a target tissue and the catheter slidably placed through the pressure apron. It should be appreciated that the above provided embodiments are merely illustrative and other embodiments, modifications, and variations of the present invention are also plausible and may be made without departing from the spirit and scope of the present invention.

What is claimed is:

1. A method for directly injecting plug forming material into body tissue comprising:
   providing a catheter including an injection tube having a first channel, a second channel, and a piercing tip;
   delivering plug forming material to the first and second channels with a pressure source;
   slidably positioning the injection tube in a pressure apron having a tissue mating surface; and
   moving the injection tube between first and second positions to form a void in the body tissue and to inject the plug forming material into the void.

2. The method of claim 1, wherein the catheter has a catheter wall that surrounds the injection tube and is coupled to the pressure apron.

3. The method of claim 1, wherein the pressure apron includes an adhesive on at least a portion of one of its surfaces.

4. The method of claim 1, wherein the pressure apron is in the form of a truncated cone.

5. The method of claim 1, wherein the pressure apron includes a biocompatible polymeric material selected from silicones, nylons, urethanes, polyamides, polyimides, elastomers, or combinations thereof.

6. A method of directly injecting plug forming material into body tissue comprising:
   providing a catheter with a lumen and a catheter piercing tip;
   coupling a pressure apron to the catheter, the pressure apron surrounding the catheter and having a tissue-mating surface adaptable to sealably engage a target tissue, the catheter slidable within the pressure apron;
   slidably positioning an injection tube within the lumen, the injection tube having at least one first channel and an injection tube piercing tip; and
   delivering plug forming material to the at least one first channel, wherein the injection tube is extendable and retractable from the lumen to form a void in the target tissue and to inject the plug forming material into the void.

7. The method of claim 6, wherein the injection tube has a second channel, the first and second channels in fluid communication with a pressure source.

8. The method of claim 6, wherein the pressure apron has an adhesive on one of its surfaces.

9. The method of claim 8, wherein the adhesive is selected from polysaccharides, cellulose, hydrogels, alginate, or combinations thereof.

10. The method of claim 6 wherein the body tissue is the myocardium.

11. A method for directly injecting plug forming material into body tissue comprising:
   providing a catheter having a lumen, at least one channel feed, and a pressure apron surrounding the lumen;
   slidably positioning an injection tube within the lumen, the injection tube having first and second channels and an injection tube piercing tip; and
   delivering plug forming material and therapeutic to the channels via the at least one channel feed,
   wherein the injection tube is extendable and retractable from the pressure apron to form a void in the body tissue and to inject the plug forming material and therapeutic into the void.

12. The method of claim 11 wherein the first and second channels are in fluid communication with a pressure source.

13. The method of claim 11 wherein the pressure apron has an adhesive on at least a portion of one of its surfaces.

14. The method of claim 13 wherein the adhesive is selected from polysaccharides, cellulose, hydrogels, alginate, or combinations thereof.

* * * * *